United States Patent [19]

Silbering et al.

[11] Patent Number: 4,696,812
[45] Date of Patent: Sep. 29, 1987

[54] THROMBIN PREPARATIONS

[75] Inventors: Steven B. Silbering, Forest Hills, N.Y.; Russell U. Nesbitt, Somerville; Mahdi B. Fawzi, Flanders, both of N.J.

[73] Assignee: Warner-Lambert Company, Morris Plains, N.J.

[21] Appl. No.: 791,836

[22] Filed: Oct. 28, 1985

[51] Int. Cl.$^4$ .................. A61K 9/70; A61K 37/48; A61L 15/00
[52] U.S. Cl. .................. 424/445; 424/94.64; 128/156; 128/DIG. 22
[58] Field of Search .................. 424/94, 28; 128/156

[56] References Cited

U.S. PATENT DOCUMENTS

| | | | |
|---|---|---|---|
| 2,433,299 | 12/1947 | Seegers | 435/188 |
| 4,138,292 | 2/1979 | Chibata et al. | 195/59 |
| 4,363,319 | 12/1982 | Altshuler | 424/28 |

OTHER PUBLICATIONS

E. F. Workman et al., *Thrombos. Haemostas.*, 1978, pp. 193-200.
Chem. Abst., 57: 11313, 1962.
Chem. Abst., 94: 36384h, 19.

*Primary Examiner*—J. R. Brown
*Assistant Examiner*—John W. Rollins, Jr.
*Attorney, Agent, or Firm*—Ronald A. Daignault

[57] ABSTRACT

Thrombin solutions can be rendered storage stable using stabilizing quantities of an anti-autolytic buffer in combination with low levels of saline and glycerol to prevent denaturation.

6 Claims, No Drawings

THROMBIN PREPARATIONS

BACKGROUND

Thrombin, a proteolytic enzyme, is essential for hemostasis. It is a principal reagent in the formation of blood clots via fibrin production. Due to its effectiveness as a clotting aid, thrombin and its preparations are useful during surgical procedures to control bleeding. While dry thrombin is available, liquid preparations are generally preferred due to handling and time considerations.

Until now, there have been no highly stable liquid thrombin preparations which are both storage stable and ready for use during surgery. This is because thrombin, when dissolved in water or saline rapidly loses its activity due to denaturation and autolysis of the thrombin protein.

THE INVENTION

It has been discovered that sterile, storage stable thrombin preparations can be produced by adding to thrombin, in a suitable medium, a stabilizing quantity of a novel buffer composition. Optionally, saline and one or more polyol stabilizers can also be employed.

In a preferred embodiment, a solution containing 1,000 U/ml (units per milliliter) Parke-Davis thrombin in 0.9% NaCl solution containing 25% (w/v) glycerol and 0.05M sodium acetate buffer, pH 5.0, was prepared. This solution, after storage at room temperature for 39 days, had a clotting time of 14 seconds when measured on a fibrometer, which represents a retention of 70% of its original activity. A freshly prepared solution of the same composition had a clotting time of 10 seconds.

ADVANTAGES

The thrombin preparations and methods of the invention have several advantages over conventional preparations and methods for assisting in blood clotting.

Unlike powdered preparations, the use of the preparation of the instant invention requires no reconstitution prior to use. Thus, measuring, mixing, sterilizing, etc. of one or more component(s) or container(s) are not considerations. The instant preparations can be used with only minimal sterilization.

Furthermore, the stability of the instant thrombin-containing materials is so great that the need for stock inventories and/or rotation of products is largely eliminated. Unlike most saline or water solutions of thrombin, which are stable for less than 1 week at 4° C., the instant preparations are designed to be stable at normal refrigeration temperatures (i.e., about 4° C. ) for 6 months or more.

It is known that high concentrations of glycerol, sucrose, and other polyols can stabilize proteins in solution. In the case of thrombin, it is known that a glycerol concentration of 67% can greatly stabilize a 1,000 u/ml thrombin solution. However, use of high glycerol concentrations is not practical in the large scale manufacture of a sterile thrombin solution because of the high viscosity of such a preparation.

Other advantages and aspects of the invention will become apparent from a consideration of the following description of the invention.

DESCRIPTION OF THE INVENTION

The invention concerns, in its broadest aspects:

I. Thrombin preparations, preferably solutions, which contain thrombin and an anti-autolytic quantity of at least one buffer.

II. Hemostatic products useful as dressings which contain the preparations of I.

III. Methods of making the thrombin preparations of I.

THE THROMBIN PREPARATIONS

The preparations made in accordance with the invention must contain, in a liquid medium, thrombin and one or more of the buffers of the invention. They may contain saline, polyols and other substances conventionally employed in thrombin preparations.

While the term "preparations" is employed, it should be noted that applicants contemplate all types of formulations in which thrombin is substantially solubilized, or in a highly dispersed form, and is present in combination with one or more of the instant buffers.

Liquid preparations are generally preferred. Solutions of thrombin are highly preferred. When a liquid formulation is made, it is generally preferred that the solvent(s) or other diluent(s) employed be sufficiently miscible with thrombin that production standards, e.g., uniformity of thrombin concentration from batch to batch, can be readily met.

The thrombin employed is commercially available. A preferred thrombin is THROMBOSTAT® powder, marketed by PARKE-DAVIS. It contains, in addition to thrombin, 30° %(w/w) glycine, 5.3% $CaCl_2 \cdot 2H_2O$ and 5.8% NaCl. It is supplied in vials containing 5,000 units, 10,000 units, and 20,000 units.

Thrombin is known to be soluble in physiological saline—i.e., a solution containing 0.9% NaCl in water. However, saline solutions with higher concentrations are contemplated as useful herein. Furthermore, the replacement of all or part of the NaCl in such solutions with one or more other suitable salts is contemplated.

Water is a preferred medium for the preparations of the invention. However, the use of one or more other diluents which do not adversely affect the solubility and/or stability of thrombin in the subject preparations can be employed.

One such diluent is glycerol. Glycerol and other polyols, such as polyaklylene glycols and preferably polyethylene glycols, are typical ingredients in many commercial thrombin-based products. Other useful polyols include mannitol, sorbitol, sucrose, glucose, and the like. Mixtures are operable.

The buffer employed in the preparations of the invention is prepared in the final aqueous formulation, and before the formulation is mixed with the thrombin. For instance, in order to prepare a formulation buffered at pH 5.3 with acetate and containing 25% glycerol in 0.9% NaCl, the glycerol-containing saline is first prepared, and the required amount of acetic acid is added. The pH is then adjusted to 5.3 with a strong sodium hydroxide solution.

Alternatively, the buffer can be prepared by adding sodium acetate and adjusting the pH with a strong acid, or, thirdly, the buffer can be prepared by adding acetic acid and sodium acetate in a mole ratio calculated to produce the desired pH.

Suitable buffer systems are those whose aqueous solutions will maintain the pH of the final thrombin solution between about 5.0 and about 8.0, with a preferred pH range of about 5.0 to 6.0. Useful buffer systems include acetate, succinate, bicarbonate, imidazole, TRIS, and the zwitterionic buffers described by N. E. Good and S. Izawa, in *Methods in Enzymol*, 24, Part B, 53 (1972); and W. F. Ferguson, K. I. Braunschweiger, W. R. Braunschweiger, J. R. Smith, J. McCormick, C. C. Wasmann, N. P. Jarvis, D. H. Bell and N. J. Good in *Anal. Biochem*, 104, 300 (1980).

Suitable reagents for use in the instant buffer systems include MES, ACES, BES, MOPS, TES, HEPES, and the like. Phosphate buffer can only be used when calcium ion is absent or in the presence of EDTA. Mixtures of such reagents can be employed.

Useful buffer systems also include acetic acid-sodium acetate, acetic acid-potassium acetate, bicarbonate, succinate, imidazole, and TRIS salts. Sodium acetate/acetic acid is a preferred reagent. Mixtures are operable.

The buffers will be present in the buffer solution, along with water and/or other suitable diluent, at total concentrations of about 0.01M to about 1M, preferably about 0.02 to about 0.2M.

The use of various other conventional additives, e.g., antioxidants, colorants, surfactants, and the like, is also contemplated. Lysine and/or other amino acids may be employed as optional ingredients.

In general, the concentration ranges for the ingredients discussed above will be within the limits set out in Table I. Percentages are based on total composition weight.

TABLE I

| Ingredient | Weight Percentage | | |
| --- | --- | --- | --- |
| | Broad | Preferred | Highly Preferred |
| Thrombin units/ml | 10-10,000 | 50-5,000 | 100-1,000 |
| Buffer solution (M) | 0.01-1.0 | 0.02-0.2 | 0.05-0.10 |
| Diluent/Solvent | — | — | — |
| Polyol | 0-50 | 10-40 | 10-25 |
| NaCl | 0-5 | 0.9-2.7 | 0.9-1.8 |

HEMOSTATS

Hemostatic materials, such as GELFOAM, SURGICEL, and AVICEL, which are presently used alone or in combination with thrombin powder or thrombin in saline, can be effectively used with the stabilized thrombin solution of the present invention. The stabilized solution can be absorbed onto the hemostatic agent and the wet pad can be packaged in a sterile manner.

Antimicrobial or antibiotic agents can also be incorporated into such pads, especially for use on burn patients, where prevention of infection is critical. In addition, surfactants and salts other than NaCl can be employed. When one or more of such additives are present, their concentrations are generally within the ranges set out in Table II.

TABLE II

| Additive | Weight Percentage | | |
| --- | --- | --- | --- |
| | Broad | Preferred | Highly Preferred |
| Surfactants | 0-2 | 0-0.5 | 0-0.2 |
| Antioxidants | 0-1 | 0-0.2 | 0-0.1 |
| Antimicrobials | 0-1 | 0-0.2 | 0-0.1 |
| Other additives e.g., salts | 0-5 | 0-3 | 0-1 |

One type of bandage suitable in the preparation of coagulants in accordance with the invention is set forth in U.S. Pat. No. 4,363,319, the disclosure of which is hereby incorporated by reference.

PRODUCTION OF THROMBIN PREPARATIONS

The thrombin formulations made in accordance with the invention are made by conventional processing techniques. The use of particular devices for mixing, adding, etc. should not be regarded as a limitation.

The order of addition of ingredients is believed to be critical, and it is generally preferred that all the ingredients except thrombin be mixed first, and the pH adjusted to 5.0, before addition to thrombin-containing powder.

EXAMPLES

The following is an example of a preferred formulation: Sodium chloride, 0.9 g, and glycerol, 25.0 g are dissolved in approximately 75 ml of distilled, deionized water. To this solution is added 0.29 ml of glacial acetic acid. The mixture is diluted to approximately 90 ml and the pH is adjusted to 5.0 with 5N sodium hydroxide. The volume of the solution is then brought to exactly 100 ml by addition of distilled, deionized water. To prepare a 1,000 unit/ml thrombin solution, 20 ml of buffered formula are added to a vial containing 20,000 units of thrombin in THROMBOSTAT® powder, or 10 ml of buffered formula are added to a vial containing 10,000 units of thrombin, 5.0 ml of buffered formula are added to 5,000 units of thrombin. The thrombin solution is shaken gently or otherwise agitated to dissolve the THROMBOSTAT® powder, and the solution is stored at 4° C. until ready for use.

The table below shows levels of thrombin activity remaining in thrombin solutions after storage at various temperatures. It is clear that the presence of a buffer significantly enhances the storage ability of thrombin preparations.

TABLE III

| | Percentage of Original Thrombin Activity After Storage at Various Temperatures | |
| --- | --- | --- |
| Composition | Temp (Storage) Time) 37° C. (11 days) | Temp (Storage Time) 25° C. (41 days) |
| THROMBIN (1,500 units/ml 0.9% saline pH 6.80 | 0 | 0 |
| THROMBIN (1,500 units/ml 25% (v/v) glycerol 0.9% NaCl pH 6.80 | 26 | 15 |
| THROMBIN (1,500 units/ml) 25% w/w glycerol 0/9% NaCl, 0.05 $\underline{M}$ acetate buffer pH 5.13 | 68 | 71 |

The thrombin activity levels were determined by measurement of clotting time on a BBL fibrometer. The source of fibrinogen was pooled human plasma diluted 1:1 with 0.9% saline. The thrombin solution was diluted 200-fold with 0.5% polyethylene glycol 8000 in imidazole buffered saline. Into a coagulation cup was added 0.2 ml of diluted plasma. This was kept at 37° C. for 3 minutes, and to this solution was added 0.1 ml of diluted thrombin solution, which had also been kept at 37° C. for 3 minutes. Clotting time was determined directly from the fibrometer reading. The number of thrombin units/ml remaining was determined from a standard curve of thrombin concentration vs. clotting time.

The data in Table IV show that while unbuffered solutions containing glycerol in saline provide some stability to low levels of solubilized thrombin, high levels of solubilized thrombin cannot be stabilized. In contrast, the degrees of stabilization of both low and high concentrations of thrombin in the buffered composition of the present invention are approximately the same, and are much greater than that provided by glycerol alone.

TABLE IV

Percentage of original activity of various concentrations of solubilized thrombin after storage at 37° C. for 2 weeks

| Composition | THROMBIN CONCENTRATION (UNITS/ML) | | |
|---|---|---|---|
| | 250 | 500 | 1,000 |
| THROMBIN 25% (w/w) glycerol 0.9% NaCl pH 6.8 | 50 | 30–40 | <30 |
| THROMBIN 25% (w/w) glycerol 0.9% NaCl 0.05 M acetate buffer pH 5.1 | 70–80 | 70–80 | 70–80 |

Reasonable variations, such as those which would occur to a skilled artisan, can be made herein without departing from the scope of the invention.

We claim:

1. A stable thrombin preparation consisting essentially of:
   (a) about 10 to about 10,000 units/ml thrombin,
   (b) an antiautolytic quantity of a buffer which maintains the pH at about 5.0 to 8.0., and
   (c) about 10 to about 40 wt % of a polyhydroxy stabilizer and about 0.9 to 2.7 wt % sodium chloride.

2. The preparation of claim 1 wherein the stabilizer is selected from the group consisting of $C_{3-12}$ polyols, and polyethylene polyols having molecular weights between about 200 to about 8,000, and mixtures thereof.

3. The preparation of claim 1 wherein the buffer is an acetate buffer.

4. A hemostat for use as a wound dressing comprising preparation of claim 1 and a substrate.

5. The preparation of claim 1, wherein the pH is about 5.3.

6. The composition claim 2 wherein the stabilizer is glycerol.

* * * * *